(12) United States Patent
Shoji et al.

(10) Patent No.: US 6,692,703 B2
(45) Date of Patent: Feb. 17, 2004

(54) NUCLEIC ACID PURIFICATION METHOD AND PURIFICATION APPARATUS

(75) Inventors: Yoshiyuki Shoji, Mito (JP); Toshiaki Yokobayashi, Hitachinaka (JP); Hiroshi Umetsu, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 140 days.

(21) Appl. No.: 09/808,157

(22) Filed: Mar. 15, 2001

(65) Prior Publication Data

US 2002/0028926 A1 Mar. 7, 2002

(30) Foreign Application Priority Data

Sep. 7, 2000 (JP) .......................................... 2000-272047

(51) Int. Cl.$^7$ ................................................ B01L 11/00
(52) U.S. Cl. ........................... 422/101; 422/69; 422/70; 422/100; 422/102; 422/52; 436/94; 436/174; 536/23.1; 536/24.1; 536/124; 536/127
(58) Field of Search ................................. 422/100, 101, 422/69, 70, 102, 52; 536/23.1, 124, 127, 24.1; 436/94, 174

(56) References Cited

FOREIGN PATENT DOCUMENTS

JP        11-266864         10/1999

OTHER PUBLICATIONS

SUPELCO Chromatography Products (1996) pp. 285 and 359–371.*

\* cited by examiner

*Primary Examiner*—James O. Wilson
*Assistant Examiner*—Patrick Lewis
(74) *Attorney, Agent, or Firm*—Dickstein Shapiro Morin & Oshinsky LLP

(57) ABSTRACT

A nucleic acid purification method and purification apparatus characterized by high washing efficiency where contamination does not occur and liquid does not remain in the nozzle tip are disclosed. The present invention provides a tip containing the solid phase capturing a nucleic acid characterized in that washing solution is fed into the tip unidirectionally from head to end.

11 Claims, 6 Drawing Sheets

NUCLEIC ACID PURIFICATION METHOD AND PURIFICATION APPARATUS

BACKGROUND OF THE INVENTION

1. Field of the Invention

The present invention relates to a nucleic acid purification method and purification apparatus and particularly to the purification method and purification apparatus suited to separate nucleic acid contained in the biological sample from the coexisting substance and to take it out.

2. Description of the Prior Art

A great number of gene technologies have been developed due to progress of molecular biology, and many pathetic genes have been separated and identified by such technologies. As a result, In the field of medical treatment as well, a technique of molecular biology is adopted in the diagnosis or inspection method. This makes it possible to perform the diagnosis which is extremely difficult so far and to achieve a substantial reduction in the number of days for inspection.

Such a progress is attributable to commercial application of gene amplification method, especially, polymerase chain reaction (called PCR method) in many respects. The PCR method makes it possible to amplify nucleic acid in the solution sequence-specifically. For this reason, it indirectly proves existence of a very small number of viruses present in the serum, by amplifying and detecting the nucleic acid as genes of these viruses. However, there are some problems when this PCR method is used for clinical applications in daily examinations. Especially, extraction of nucleic acids in the pretreatment process and purification process are important to maintain accuracy. Some techniques have been proposed regarding purification of nucleic acid.

According to the method disclosed in Japanese Official Patent Gazette 266864/1999, a nucleic acid capturing tip incorporating solid phase containing silica is used to extract nucleic acid automatically. A nozzle tip is mounted on the liquid suction/discharge movable nozzle and sucks from the bottle the binding enhancer to accelerate nucleic acid to be bound onto said solid phase. Then it sucks the sample containing nucleic acid from the specimen vessel and discharge their mixture into the reaction vessel. After the mixture has been discharged, the nozzle tip is discarded, and a new nucleic acid capturing tip is mounted in position. The mixture is sucked from inside said reaction vessel and discharged into the nucleic acid capturing tip connected to the liquid suction/discharge movable nozzle. Then nucleic acid in the sucked mixture is bound with the solid phase in the nucleic acid capturing tip, and liquid in said nucleic acid capturing tip is discharged. Then washing solution discharged in the washing vessel is sucked into said nucleic acid capturing tip, and said washing solution is discharged from said nucleic acid capturing tip. Said solid phase bound with nucleic acid and interior of said nucleic acid capturing tip are washed. Further, eluent is sucked into the said nucleic acid capturing tip after having been washed, and eluent containing the nucleic acid separated from said solid phase is discharged into a vessel for purified product.

According to the method disclosed in Japanese Official Patent Gazette 266864/1999, when there is reaction between the sample containing nucleic acid and various types of reagents, the sample containing nucleic acid is sucked from the specimen vessel or reaction vessel and is dispensed into the targeted reaction vessel. So said sample may scatter up to the mechanism holding the nozzle tip, and may cause contamination which will give a serious influence to nucleic acid purifying performances.

The solid phase bound with nucleic acid and the interior of the nucleic acid capturing tip are washed. The washing solution discharged into special-purpose vessel is sucked into said tip and is discharged into the special-purpose vessel. This process is repeated, resulting in a poor cleaning efficiency. Further, if washing solution remains in the solid phase of said tip, the next eluent concentration will be affected to deteriorate nucleic acid purifying performances.

SUMMARY OF THE INVENTION

The object of the present invention is to provide a nucleic acid purification method and purification apparatus which ensures excellent washing efficiency without causing contamination or liquid remaining in the nozzle tip.

To achieve the above object, the following means are provided:

In a nucleic acid purification method wherein a nucleic acid capturing tip incorporating the solid phase containing a nucleic acid capturing agent is used to allow said solid phase to capture a nucleic acid and to extract the nucleic acid, the present invention is characterized in that washing solution is fed in the tip containing the solid phase capturing said nucleic acid unidirectionally from the head to the end.

Silica can be cited as an specific example of said nucleic acid capturing agent. Fine particles mainly composed of silica, fibers and fibrous wool are preferred as nucleic acid capturing agent according to the present invention. Silica wool made of silica fiber is particularly preferred.

Said nucleic acid purification method is characterized in that a branch for the washing solution flow path is provided in the flow path leading to the nucleic acid capturing tip, and washing solution is poured therein. The flow path can be shortened by switching the washing agent flow path. This makes it possible to reduce the size of the nucleic acid purification apparatus.

In said nucleic acid purification method, it is preferred to provide a special-purpose flow path to feed washing solution to the nucleic acid capturing tip. System operation and maintenance are facilitated by providing a simple washing solution flow path to the tip, without providing a washing solution switching flow path.

In said nucleic acid purification method, it is preferred to feed air into the flow path. This makes it possible to quickly remove from the tip the washing solution containing impurities included in nucleic acid sucked by the capturing agent.

In said nucleic acid purification method, it is preferred that discharge of washing solution and feed of air be repeated alternately. This ensures effective removal of washing solution remaining in the tip.

The present invention is characterized by a nucleic acid purification apparatus wherein a nucleic acid capturing tip incorporating the solid phase containing a nucleic acid capturing agent is used to allow said solid phase to capture a nucleic acid and to extract the nucleic acid;

said nucleic acid purification apparatus characterized in that washing solution is fed in the tip containing the solid phase capturing said nucleic acid unidirectionally from the head to the end.

In the above nucleic acid purification apparatus, it is preferred that the flow path leading to said nucleic acid capturing tip be provided with a branch for a washing solution flow path, and a means to supply washing solution be provided. The flow path can be shortened by switching the washing agent flow path. This makes it possible to reduce the size of the nucleic acid purification apparatus. In above nucleic acid purification method, it is preferred to provide a special-purpose flow path to feed washing solution to the nucleic acid capturing tip.

System operation and maintenance are facilitated by providing a simple washing solution flow path to the tip, without providing a washing solution switching flow path.

In above nucleic acid purification method, it is preferred to provide a means of feeding air into the flow path.

This makes it possible to quickly remove from the tip the washing solution containing impurities included in nucleic acid sucked by the capturing agent.

In said nucleic acid purification method, it is preferred that discharge of washing solution and feed of air be repeated alternately. This ensures effective removal of washing solution remaining in the tip.

The present invention is characterized by a nucleic acid purification apparatus wherein a nucleic acid capturing tip incorporating the solid phase containing a nucleic acid capturing agent is used to allow said solid phase to capture a nucleic acid and to extract the nucleic acid;

said nucleic acid purification apparatus comprising;
- a nucleic acid capturing tip incorporating the solid phase containing a nucleic acid capturing agent,
- a liquid suction/discharge movable nozzle in contact with said nucleic acid capturing tip in a removable manner,
- a treatment solution capable of storing a mixture between the substance to promote capturing of nucleic acid by said solid phase and sample containing nucleic acid,
- a means for feeding washing solution into the tip containing the solid phase capturing said nucleic acid unidirectionally from the head to the end,
- a means for supplying eluent to said nucleic acid capturing tip,
- a top removing means for removing said nucleic acid capturing tip from said liquid suction/discharge movable nozzle subsequent to discharge of eluent from said nucleic acid capturing tip to a purified product vessel, and
- a purified product vessel to receive purified nucleic acid products.

The present invention provides a nucleic acid purification method and purification apparatus characterized by high washing efficiency where contamination does not occur and liquid does not remain in the nozzle tip.

DESCRIPTION OF THE PREFERRED EMBODIMENTS

Figure 1:
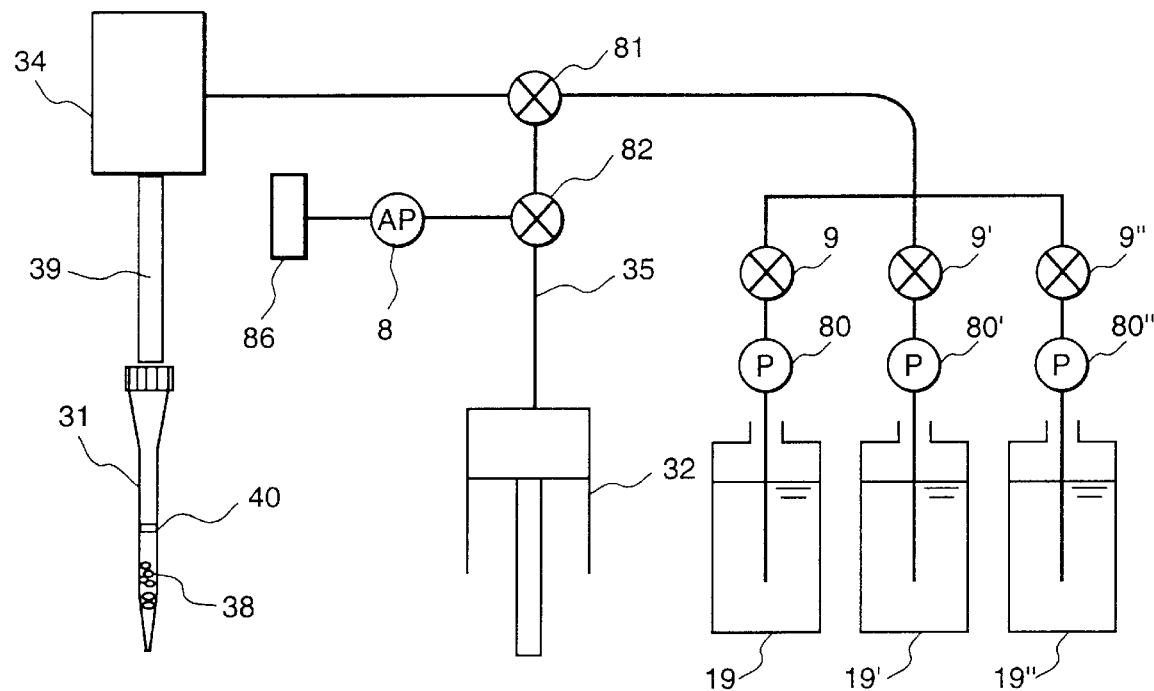
FIG. 1 is a drawing representing the schematic configuration of the dispenser provided with a flow path switching valve in a nucleic acid purification apparatus according to the present invention.
Figure 2:
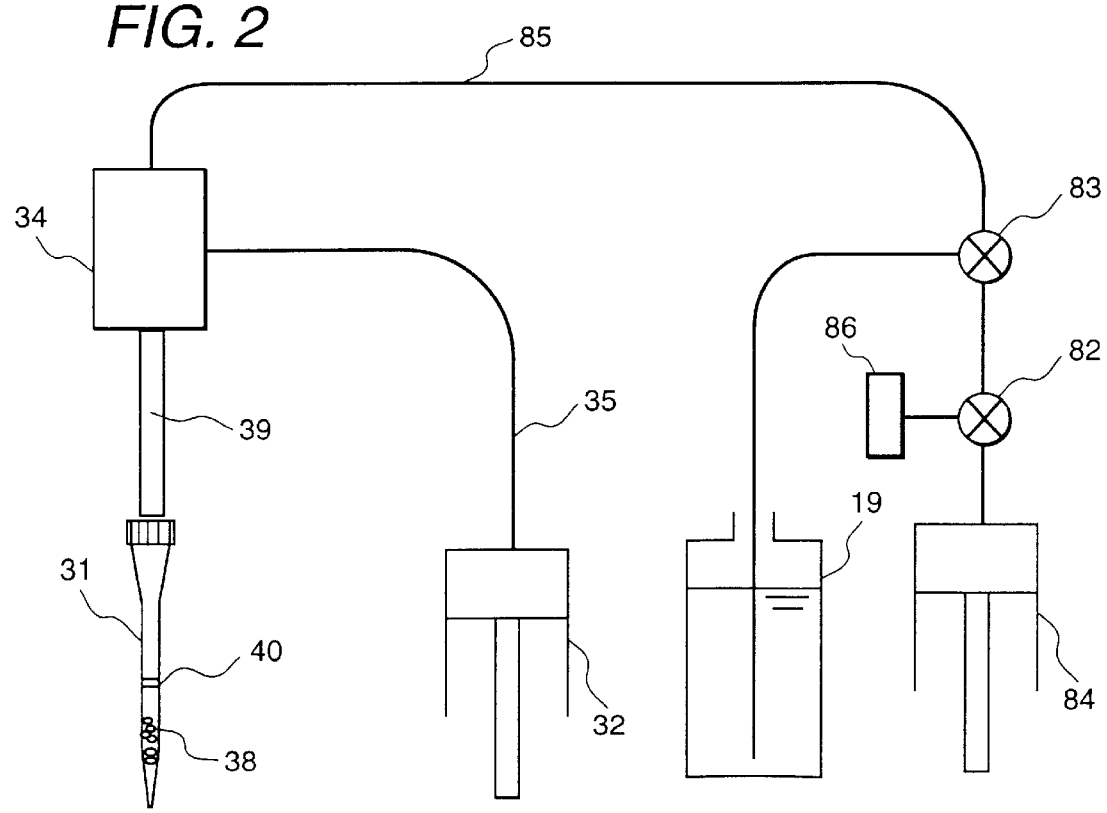
FIG. 2 is a drawing representing the schematic configuration of the dispenser provided with a flow path specifically designed for washing solution in a nucleic acid purification apparatus according to the present invention.
Figure 3:
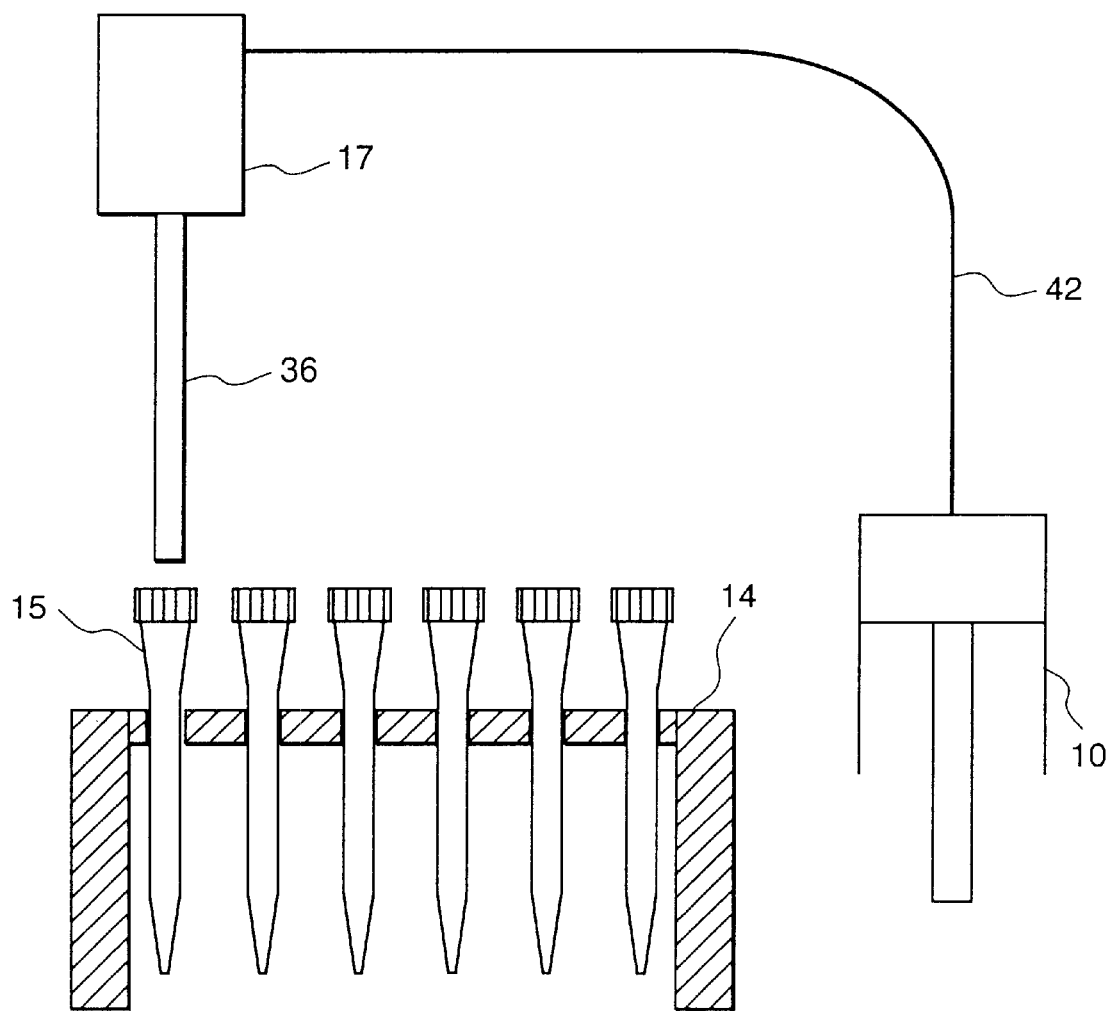
FIG. 3 is a drawing illustrating how to install the liquid dispensation tip on the nozzle in a nucleic acid purification apparatus according to the present invention.
Figure 4:
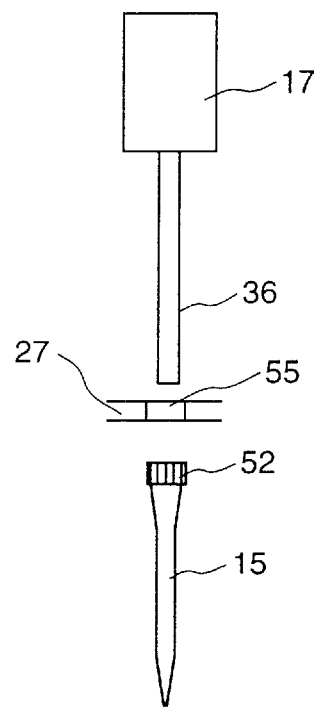
FIG. 4 is a drawing illustrating how to remove the tip form the nozzle in a nucleic acid purification apparatus according to the present invention.
Figure 5:
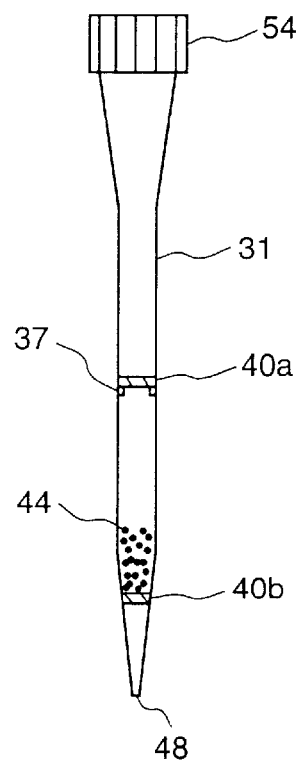
FIG. 5 is a drawing representing the schematic configuration of a nucleic acid capturing tip according to the present invention.
Figure 6:
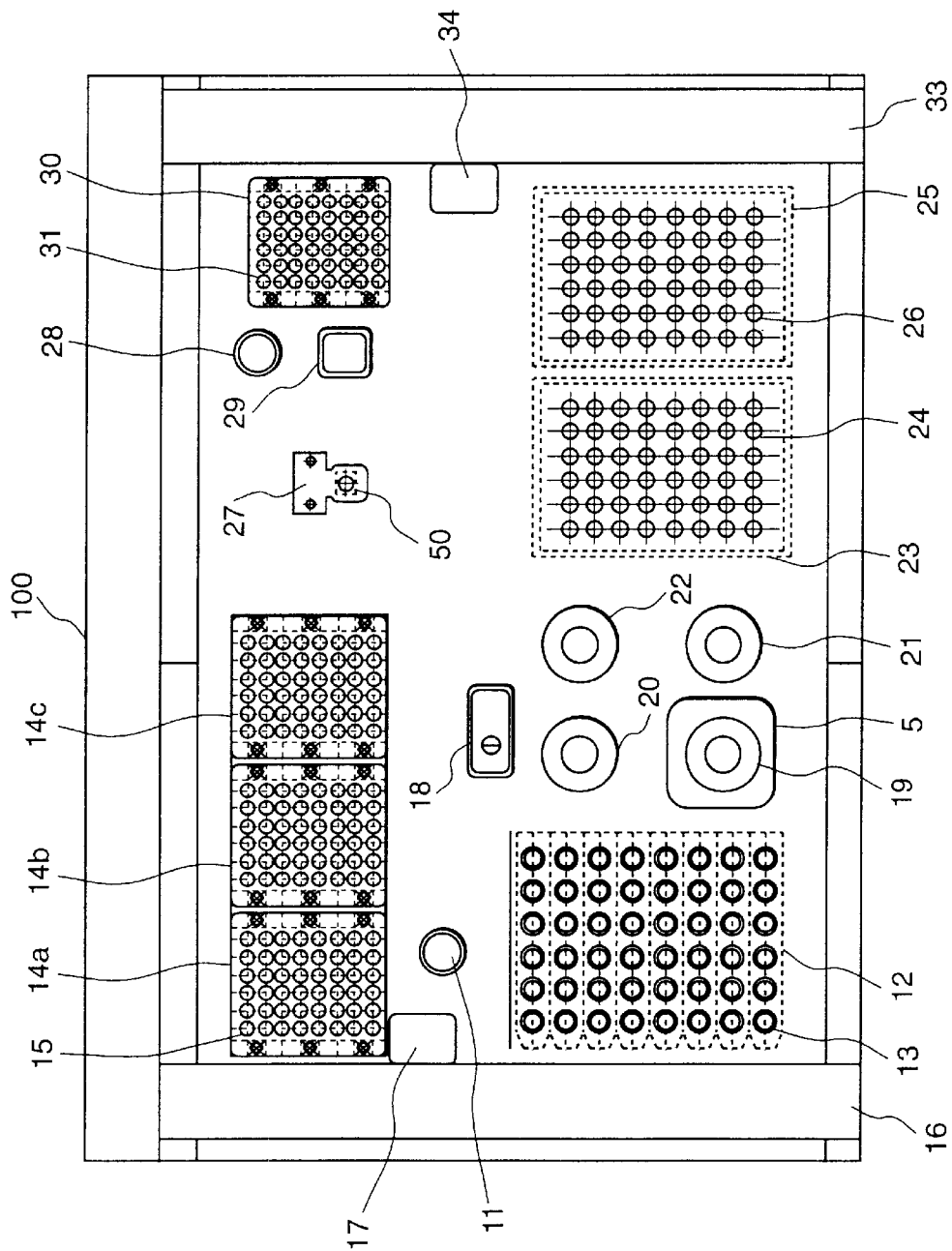
FIG. 6 is a plan representing one embodiment of a nucleic acid purification apparatus according to the present invention.
Figure 7:
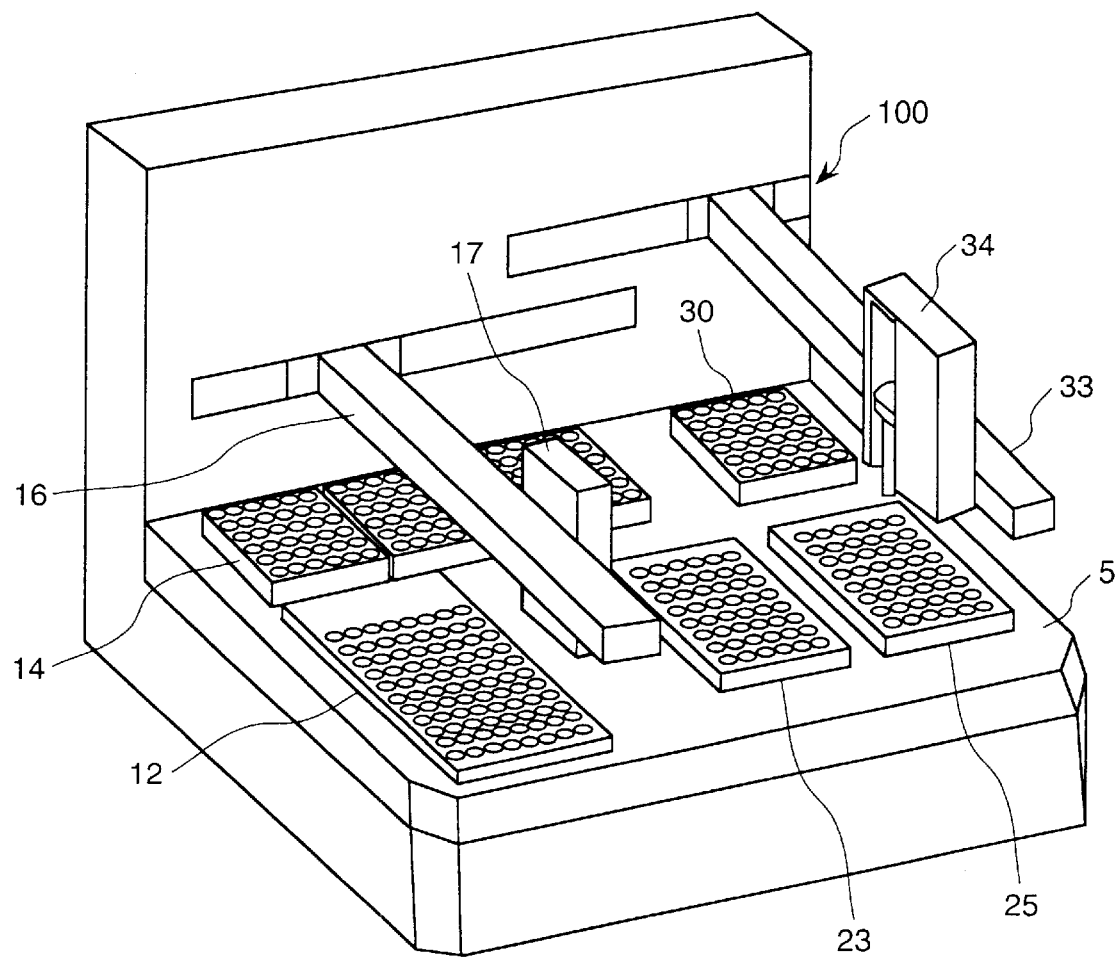
FIG. 7 is a schematic external view representing one embodiment of a nucleic acid purification apparatus according to the present invention.
Figure 8:
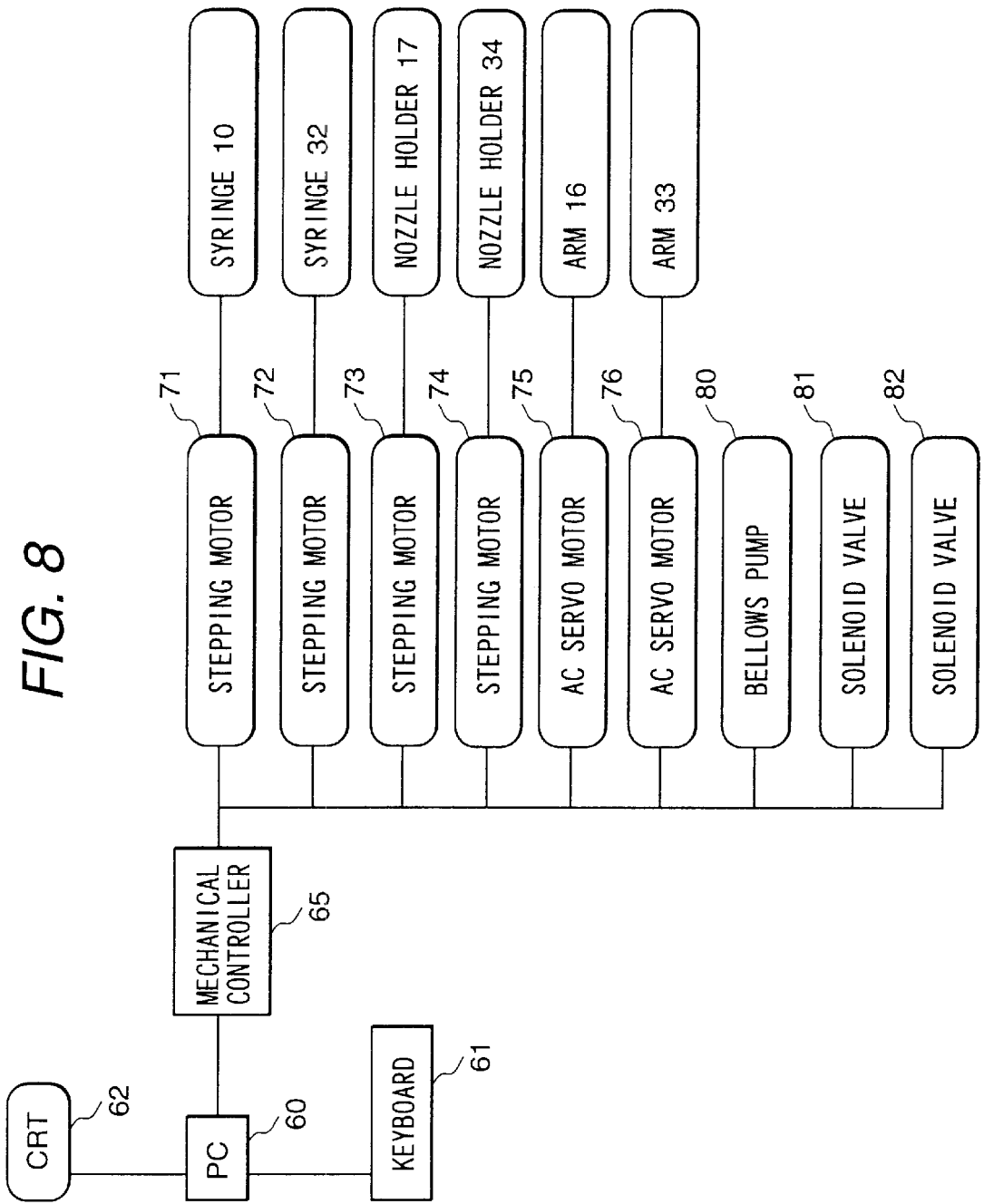
FIG. 8 is a block diagram representing the configuration of the electric system in one embodiment of a nucleic acid purification apparatus according to the present invention.

The following describes a nucleic acid purification apparatus as one embodiments according to the present invention with reference to FIGS. 1 to 8: This embodiment shows an example of applying the prevent invention to the washing process. FIG. 6 is a plan representing the modifier as one embodiment of the present invention. FIG. 7 is an external view representing it and FIG. 8 is a block diagram of the electric system. FIGS. 1 and 2 are schematic views representing the dispenser connected with a nucleic acid capturing tip and washing solution washing mechanism. FIG. 3 is a drawing illustrating how to install the liquid dispensation tip. FIG. 4 is an illustrative drawing to show how to remove the tip. FIG. 5 is a drawing to show the nucleic acid capturing tip configuration.

In FIGS. 6 and 7, Nucleic acid purification apparatus 100 is equipped with two arms 16 and 33 movable in the horizontal direction (X direction). The arm 16 has is equipped with a nozzle holder 17 holding a dispensing nozzle 36 (FIG. 3) along the length of arm 16 in such a way that it can be moved in horizontal direction (Y direction ). The other arm 33 is provide with a nozzle holder 34 to hold the liquid suction/discharge movable nozzle 39 (FIG. 1) along the length of arm 33 in such a way that it can be moved in horizontal direction (Y direction ). Nozzle holders 17 and 34 can be moved in the vertical direction (Z direction) with respect to the corresponding arms 16 and 33. The area where the arm 16 moves in the horizontal direction partly overlaps with that where the arm 33 moves in the horizontal direction. Therefore, these arms are installed at different positions.

Three tip racks 14a, 14b and 14c with many unused dispensation tip 15 mounted thereon are set on specified areas of the working surface 5 of the main unit base. As shown in FIG. 3, these tip racks 14 are provided with holes through which dispensation tips 15 are inserted. The end of the dispensation tip is designed in a box structure located at such a height that does not contact the working surface 5 or tip rack bottom.

Further, tip rack 30 with many unused nucleic acid capturing tips 31 mounted thereon is set on a specified area of the working surface. The tip rack 30 is designed in the same form as the tip rack 14. In this example, a maximum of 48 nucleic acid capturing tips 31 can be held on the tip rack 30.

Specimen rack 12 holding multiple specimen vessels 13 storing the specimen to be treated, namely, the sample containing nucleic acid is set at a specified area of the working surface 5. In this example, six specimen vessels 13 can be held by each specimen rack 12. Eight or more can be set on the specimen rack 12.

Vessel rack 23 holding many unused vessels 24 can be set at a specified area of the working surface 5. Vessel rack 23 can hold a maximum of 48 treatment vessels 24. Further, vessel rack 25 holding many unused purified product vessel 26 is set on a specified area of the working surface 5. This purified product vessel is used to recover the liquid containing purified nucleic acid for each sample. In this example, vessel rack 25 can hold a maximum of 48 purified product vessels 26.

The working surface 5 is equipped with;

a liquid receiver 11 which receives water discharged from dispensing nozzle 36 at the time of priming and serves as a home position of the dispensing nozzle 36, a washing unit 18 to wash dispensation tip 15 to perform dispensation function, a tip remover 27 to remove from each nozzle a dispensation tip 15 connected to the dispensing nozzle 36 and the nucleic acid capturing tip 31 connected to the liquid suction/discharge movable nozzle 39, a liquid receiver 28 to receive water discharged from the liquid suction/discharge movable nozzle 39 at the time of priming and serves as a home position for said liquid suction/discharge movable nozzle 39, and a waste liquid port 29 to discharge unwanted liquid from the nucleic acid capturing tip 31.

Further, a washing solution bottle 19,19',19" containing a washing solution bottle 19,19',19" to store washing solution to wash solid phase in the nucleic acid capturing tip 31, an eluent bottle 20 which stores eluent to elute nucleic acid bound with solid phase, a dilutions bottle 21 storing dilutions, and a binding enhancer bottle 22 storing binding enhancing solution which enhances nucleic acid binding with solid phase are set at each specified position of working surface 5.

Syringe pump 10 shown in FIG. 3 and syringe pump 32 shown in FIG. 1 are each mounted on the main unit base. Liquid suction and discharge operation are controlled independently for each pump. As shown in FIG. 3, the dispensing nozzle 36 held by the nozzle holder 17 is connected to the liquid suction/discharge cylinder pump 10 through flexible tube 42. The dispensing nozzle 36 and tube 42 are filled with purified water. The syringe pump 10 is connected to a purified water supply source (not illustrated). As shown in FIG. 1, the liquid suction/discharge movable nozzle 39 held by the nozzle holder 34 is connected to the syringe pump 32 through the flexible tube 35. The liquid suction/discharge movable nozzle 39 and tube 35 are filled with purified water. The syringe pump 32 is connected to a purified water supply source (not illustrated). The dispensation tip 15 is connected to dispensing nozzle 3 and the nucleic acid capturing tip 31 is connected to liquid suction/discharge movable nozzle 39 by lowering each nozzle and fitting the tip to the end of the nozzle on respective corresponding tip racks 14 and 30. Furthermore, tip remover 27 is used to from each nozzle the dispensation tip 15 connected to the dispensing nozzle 36 and the nucleic acid capturing tip 31 connected to the liquid suction/discharge movable nozzle 39. As shown in FIGS. 6 and 4, the tip remover 27 has a plate-formed member at a specified height, and this member has a slit 55 having a width which is smaller than the outer diameters of the head of the dispensation tip 15 and head 54 of the nucleic acid capturing tip 31 and is greater than those of the dispensing nozzle 36 and liquid suction/discharge movable nozzle movable nozzle 39. When heads 52 and 54 of tips are lower than the slit 55, nozzles 36 and 39 are moved horizontally to be inserted into the slit, and the nozzle holders 17 and 34 are moved upward. Then heads 52 and 54 contact the bottom of the plate-formed member. Tips 15 and 31 are pulled out of the nozzle by further rise of the nozzle holder. The pulled out tip is dropped into the tip outlet 50 (FIG. 6), and is recovered and put into a recovery box (not illustrated).

In FIG. 1 nozzle holder 34 holds capturing tip 31 by means of movable nozzle 39 for supplying and discharging liquid. The nozzle holder 34 is communicated with piping through solenoid valve 81 and with syringe 32 through piping 35 by means of air suction switching valve 82. When the nozzle holder and the tip 31 are washed with air, a certain volume of air is injected into the nozzle holder and the tip. In order to increase the volume of air, switching valve is operated so as to communicate air pump 8 with the nozzle holder and the tip. As a result, any amount of air is supplied to the holder and tip by means of the air pump 8.

Bottles 19, 19', 19" are connected to solenoid valve 81 through switching valves 9, 9', 9" to select washing liquid in the bottles, The liquids in the bottles have different compositions and are kept at different temperatures so that the adequate washing liquid is supplied through bellows pumps 80, 80', 80" to the tip 31.

FIG. 8 shows the configuration of the electric system of the nucleic acid purification apparatus given in FIG. 6. A personal computer (PC) as operation controller is connected with a keyboard 61 serving as an operation panel to enter operation conditions and specimen information, a CRT62 as a display unit to display input information and alarm information, and a mechanical controller 65 to control each mechanism of the purification apparatus. The mechanical controller 65 controls;

a piston drive stepping motor 71 to allow the syringe pump 10 to perform suction and discharge operation, a piston drive stepping motor 72 to allow the syringe pump 32 to perform suction and discharge operation, a stepping motor 73 to move the nozzle holder 17 in the horizontal and vertical directions, a stepping motor 74 to move the nozzle holder 34 in the horizontal and vertical directions, an a.c. servo motor to move the arm 16 in the horizontal direction, an a.c. servo motor 76 to move the arm 33 in the horizontal direction a bellows pump 80 for washing solution discharge, a solenoid valve 81 to switch the washing solution flow path, and a solenoid valve 82 to feed air into the syringe pump 3.

Each portion of the purification apparatus is operated according to the specified program.

FIG. 5 shows the configuration of one embodiment of nucleic and capturing tip 31. The nucleic acid capturing tip 31 has the inner diameter which ensures that the head 54 is fitted to the end of the movable nozzle 39 in an air tight state. It is configured to ensure that the inner diameter is gradually reduced toward the end 48 on the lower portion. The tip 31 is composed of transparent or translucent plastics. A disk formed blocking member 40b to prevent outflow of the solid phase is provided on the end of the tip 31 by insertion through press fitting, and a disk formed blocking member 40a to prevent outflow of the solid phase is provided on the head 54.

These blocking members 40a and 40b equipped with many holes to allow easy passage of liquid and air. These holes have a size that blocks the outflow of solid phase. Polyvinyliden fluoride having hydrophilic properties with little non-specific adsorption is used as a material for blocking members 40a and 40b. This material is capable of reducing non-specific adsorption of protein and nucleic acid, and has a small impact on degree of nucleic acid purification and yield. The underside of blocking member 40a is provided with multiple protruded auxiliary insertion guides 37 to facilitate insertion in to the tip 31. A chamber sandwiched between the blocking members 40a and 40b is filled with powder 44 of flint glass (by Wako Pure Chemicals Industries, Ltd.) as a solid phase. This flint glass as a high content of silica having a nucleic acid capturing effect.

The following describes the operation for nucleic acid purification in an embodiment given in FIG. 6. Before the operation for purification of the sample containing the nucleic acid is started, pBR322DNA (by Fermentas) as a purified product available on the market was treated by tris-EDTA buffer solution (pH 7.5, TE buffer) to a specified concentration. The resulting solution is put into the specimen vessel 13, and was held by the specimen rack. It is set in the specimen area on the purification apparatus 100 given in FIG. 6. A tip rack 14 with dispensation tip 15, a tip rack 30 with nucleic acid capturing tip 31, a vessel rack 23 with bottles 19, 20, 21 and 22 and a treatment vessel 24, and a vessel rack 25 with purified product vessel 26 are set at specified positions. Then operation of purification apparatus 100 was started.

First, nozzle holder 17 was operated and the dispensing nozzle 36 positioned at the liquid receiver 11 moves onto the tip rack 14a for specimen. The first dispensation tip is fitted with the dispensing nozzle 36. Then the mounted dispensation tip 15 moves onto the binding enhancer bottle 22, and is lowered into said bottle. A specified amount of guanine hydrochloride solution is sucked into the dispensation tip 15 through suction by syringe pump 10. The dispensation tip is raised from inside the binding enhancer bottle 22, and a small amount of air is sucked into the end of the dispensation tip to moved it to the washing unit 18. Washing solution is sprayed to the outer wall of the dispensation tip to wash the outer wall of the dispensation tip 15. Then the dispensing nozzle 36 moves to the first specimen vessel 13 on the specimen rack 12, and the dispensation tip 15 is lowered into the specimen vessel. A specified amount of specimen is sucked into the dispensation tip 15 by the suction of syringe pump 10. As a result of these steps, layers of guanine hydrochloride solution, air and sample solution containing nucleic acid are formed in the dispensation tip 15.

The dispensation tip 15 having sucked the specimen moves to the first treatment vessel 24 on the vessel rack 23. Specimen in the dispensation tip 15 and the full amount of guanine hydrochloride solution are discharged into the treatment vessel 24. After the step of discharging, the full amount of discharged solution is sucked into the same dispensation tip 15. Further, the step of discharging into the first treatment vessel 24 is performed once or more times. Thus, the sample containing nucleic acid is blended with binding enhancer. After that, the dispensing nozzle 36 moves to the tip remover 27, and used dispensing tip 15 is taken out of the dispensing nozzle 36 according to the operation of removal described above. Then the dispensing nozzle 36 is returned to the liquid receiver 11. A specified amount of purified water is discharged from the dispensing nozzle 36. Then a small amount of air is sucked into the end of dispensing nozzle 36. The system waits until the next command of the next operation for nozzle holder 17 is received.

While blending operation is performed by dispensing nozzle 36, liquid suction/discharge movable nozzle 39 moves from the liquid receiver 28 to the first nucleic acid capturing tip 31 on the tip rack 30 by the operation of the arm 33 and nozzle holder 34, and nucleic acid capturing tip 31 is fitted to the end of movable nozzle 39. Then the movable nozzle 39 with the nucleic acid capturing tip 31 bound thereto moves to the first treatment vessel 24 on the vessel rack 23, and nucleic acid capturing tip 31 is lowered. The full amount of the mixture between specimen contained in the first treatment vessel and binding enhancer is sucked into the nucleic acid capturing tip 31 by suction of the syringe pump 32. This allows the mixture to contact the surface of the glass powder 44 as solid phase in the tip 31. Then the sucked mixture is discharge and returned into the first treatment vessel 24, and the discharged mixture is again sucked into the same nucleic acid capturing tip 31. The step of discharging and sucking of this mixture is repeated several times to increase the number of the contacts between solid phase surface and mixture, thereby improving nucleic acid suction efficiency by solid phase.

After suction and discharge are repeated a specified number of times, the full amount of mixture is sucked into the first nucleic acid capturing tip 31 in the final phase. Said tip 31 moves to waste liquid port 29, and liquid remaining after suction of nucleic acid is discharge into the waste liquid port 29 by syringe pump 32. Then the flow path switching solenoid valve 81 is actuated to connect between the washing solution flow path and nucleic acid capturing tip 31. Then the belows pump 80 for washing water suction is operated to inject washing solution into said tip. This step is not particularly restricted to the bellows pump. Any device having the liquid feed function such as a syringe pump can be used in this step.

Said washing solution is fed unidirectionally from head (upstream) to end (downstream). The washing solution having passed through said tip is continuously discharged from the underside of the cover to the waste liquid port 29. After discharge of washing solution, flow path switching solenoid valve 81 is actuated to switch the flow path to the syringe 32. Then the air suction switching solenoid valve 82 is actuated to allow air to be fed into the syringe pump 10. After that, the syringe 32 is operated to allow air to be sucked in the syringe. Since a nucleic acid capturing solid phase giving resistance to the nucleic acid capturing tip 31 is installed, most of air is sucked through the less resistant flow path which is opened by the solenoid valve 82. Then the solenoid valve 82 is closed to stop air suction. Then the syringe 32 is actuated in the direction to discharge air into the nucleic acid capturing tip 31 and to discharge all the remaining liquid from said tip. The inner wall of the nucleic acid capturing tip 31 and the surface of the solid phase are washed by this washing process.

The step of washing can be repeated to increase the washing efficiency further. The same step is taken for the second washing. If required, a third washing operation can be performed. The nucleic acid capturing tip 31 having discharged washing solution to the waste liquid port 29 and completed the step of washing moves to the liquid receiver 28 to wait for the next command. The washing solution used herein is aqueous solution of ethanol of 70% concentration.

In the nucleic acid elution process, the dispensing nozzle 36 moves to the first dispensation tip on the tip rack 14c, and the dispensation tip 15 is fitted into the end of said nozzle 36 by lowering of the dispensing nozzle 36. The dispensing nozzle 36 connected with the dispensation tip moves to the eluent bottle. Pure water as eluent is contained in the eluent bottle 20. eluent bottle 20 is preferred to be heated. The amount of eluent to be used several times is sucked in the dispensation tip 15 by the suction of the syringe pump 10. Then the dispensation tip 15 moves to the first treatment vessel 24 on the vessel rack 23, and the amount of eluent for one-time use is discharged into the first treatment vessel 24 from the dispensation tip 15 by the pushing operation of the syringe pump 10. The dispensation tip 15 holding the remaining eluent moves to the liquid receiver 11 and is placed in the wait mode therein.

The nucleic acid capturing tip 31 waiting at the liquid receiver 28 travels to the first treatment vessel 24 on the vessel rack 23 to suck eluent of the first treatment vessel 24 into the nucleic acid capturing tip 31. This causes eluent to contact the solid phase, so that nucleic acid adsorbed on the solid phase is eluted in eluent. After eluent sucked into the tip 31 is discharged into the original treatment vessel 24, it is again sucked into the same tip 31. This step is repeated a specified number of times. In the final step, nucleic acid capturing tip 31 sucking and holding eluent moves to the first purified product vessel 26 on the vessel rack 25. Eluent in the nucleic acid capturing tip 31 is pushed by syringe pump 32 to be discharged in the first purified product vessel 26. Thus, eluent containing nucleic acid eluted from the solid phase is recovered and put in the purified product vessel 26. After eluent discharge, the nucleic acid capturing top 31 moves to the liquid receiver 28 and is placed in the wait mode. Then the dispensation tip 15 holding eluent moves from the liquid receiver 11 to the first treatment vessel 24 to discharge the amount of eluent for next one step into said treatment vessel.

Then the nucleic acid capturing tip 31 waiting at the liquid receiver 28 travels to the first treatment vessel 24 to suck eluent of the first treatment vessel 24 into the nucleic acid capturing tip 31. After elution of nucleic acid in the same manner as described above, eluent containing nucleic acid is recovered and put into the first purified product vessel 26. Such a step of eluent supply by the dispensation tip 15 and elution by the nucleic acid capturing tip 31 are repeated for a specified number of times, for example, three times. After eluent discharge, the dispensation tip 15 moves to the tip remover 27, and the used dispensation tip 15 is removed from the dispensing nozzle 36. The dispensing nozzle 36 with dispensation tip removed moves to the liquid receiver 11, and discharges water from the nozzle end. Then it sucks a very small amount of air into the nozzle end waits at that position. After completing discharge of nucleic acid-containing eluent into the purified product vessel 26 several times, the nucleic acid capturing tip 31 travels to the tip remover 27 to remove the used nucleic acid capturing tip 31 from the movable nozzle 39. The movable nozzle 39 with the nucleic acid capturing tip removed moves to the liquid receiver 28, and discharge a specified amount of water from the nozzle. After that, it sucks a very small amount of air into the nozzle end, and waits at that position.

All the steps of nucleic acid purification for the first specimen are now complete. After that, purification apparatus 100 given in FIG. 6 continues nucleic acid purification of the second specimen and later, but the steps consist of repetition of the steps described above. The first dispensation tip on each of dispensation racks 14*a*, 14*b* and 14*c*, the first nucleic acid capturing tip on the tip rack 30, the first treatment vessel 24 on the vessel rack 23, and the first purified product vessel on the vessel rack 25 were used for the first specimen. Their second components are used for the second specimen. The components are changed for the third specimen and later in the similar manner. Thus, purified and recovered specimen containing the nucleic acid are recovered and put into the row of purified product vessels on the vessel rack 25 according to the order of the specimens. New ones are used as these components for each specimen, thereby preventing mutual contamination among specimens. This embodiment shows the case where one washing solution flow path is provided for each dispensing nozzle. Multiple washing solution flow paths can be installed by increasing the number of switching valves.

The following describes anther embodiment of the washing methods according to the present invention: FIG. 2 shows the configuration where washing solution is directly into the liquid suction/discharge movable nozzle 39 without any branch provided in the in the flow path. Configuration of other parts is the same as that of the embodiment described above. In the final phase after suction and discharge have been performed a specified number of times, all the mixture is sucked into the first nucleic acid capturing tip 31, and said tip 31 moves to the waste liquid port 29. The liquid remaining after adsorption of the nucleic acid is discharged into the waste liquid port 29 by the syringe pump 32.

Then the washing solution on-off valve 83 is actuated to connect between the washing solution vessel 19 and syringe pump 84. This is followed by the operation of the syringe pump 84 to suck washing solution into the syringe pump. Then the washing solution on-off valve 83 is again operated to connect the syringe pump 84 to the nucleic acid capturing tip 31. Then the syringe pump 84 is driven in the opposite direction to feed washing solution into said tip. Said washing solution is discharged unidirectionally from above said tip downward. Washing solution having passed through said tip is continuously discharged from the underside of the tip to the waste liquid port 29. After completion of washing solution discharge, air suction switching valve 82 is actuated to to enable air to be taken in. The syringe pump 84 is driven again to suck air into the syringe pump. The air suction switching valve 82 is actuated to connect the syringe pump 84 to the nucleic acid capturing tip 31. The syringe pump 32 is again driven in the opposite direction discharge air in the nucleic acid capturing tip 31, thereby discharging all the liquid remaining in said tip. This embodiment shows an example of one washing solution flow path provided for one dispensing nozzle. It is also possible to provide multiple washing solution flow paths. Numeral 85 denotes a flow path specifically designed for washing solution, and 86 shows a air filter.

What is claimed is:

1. A nucleic acid purification apparatus comprising:
   a nucleic acid capturing tip incorporating a solid phase containing a nucleic acid capturing agent, said tip being provided with a solution-path at its top of said tip which allows a nucleic acid containing solution to be sucked and discharged therethrough for extraction of nucleic acid; and
   a flow-path for introducing a washing solution into said tip therethrough, said flow-path being provided on a part of said tip different from said top, wherein said washing solution is discharged from said top.

2. A nucleic acid purification apparatus according to claim 1 characterized in that a means is provided to repeat discharge of washing solution and feed of air alternately.

3. A nucleic acid purification apparatus according to claim 1, further comprising a pump for pressurized feeding of said washing solution into said tip, said pump being controlled by a mechanical control unit.

4. A nucleic acid purification apparatus according to claim 1, further comprising a nozzle connectable to said tip of said part different from said top, said nozzle being able to feed said washing solution into said tip, wherein an eluent is sucked or discharged through said top after feeding said washing solution, and said tip and said nozzle are kept mutually connected from the beginning of sucking of said nucleic acid containing solution to the end of discharging of said eluent.

5. A nucleic acid purification apparatus according to claim 1, further comprising a nozzle for sending air into said tip after feeding said washing solution into said tip.

6. A nucleic acid purification apparatus according to claim 5, wherein said eluent is sucked and discharged through said top after sending said air.

7. A nucleic acid purification apparatus comprising:
a nucleic acid capturing tip incorporating a solid phase containing a nucleic acid capturing agent, said tip being provided with a solution-path at its top of said tip which allows a nucleic acid containing solution to be sucked and discharged through said top, said solution-path being retained by a part of said tip different from said top; and
a nozzle for feeding a washing solution into said tip, wherein said nozzle feeds said washing solution into said tip after discharging of said nucleic acid containing solution.

8. A nucleic acid purification apparatus according to claim 7, further comprising a pump being controlled by a mechanical control unit for pressurization of said washing solution.

9. A nucleic acid purification apparatus according to claim 7, wherein an eluent is sucked or discharged through said top after feeding said washing solution, and said tip and said nozzle are mutually connected from the beginning of sucking of said nucleic acid containing solution to the end of discharging of said eluent.

10. A nucleic acid purification apparatus according to claim 7, wherein said nozzle sends air into said tip after feeding said washing solution.

11. A nucleic acid purification apparatus according to claim 10, wherein said tip sucks and discharges said eluent after sending said air.

* * * * *